US006326208B1

United States Patent
Denney

(10) Patent No.: US 6,326,208 B1
(45) Date of Patent: Dec. 4, 2001

(54) ASSAY FOR TOTAL AND DIRECT BILIRUBIN

(75) Inventor: Jerry W. Denney, Lachine (CA)

(73) Assignee: Synermed International Inc., Montreal (CA)

( * ) Notice: Subject to any disclaimer, the term of this patent is extended or adjusted under 35 U.S.C. 154(b) by 0 days.

(21) Appl. No.: 09/463,131

(22) PCT Filed: Jul. 16, 1998

(86) PCT No.: PCT/US98/14779

§ 371 Date: Jan. 18, 2000

§ 102(e) Date: Jan. 18, 2000

(87) PCT Pub. No.: WO99/04258

PCT Pub. Date: Jan. 28, 1999

Related U.S. Application Data

(60) Provisional application No. 60/052,844, filed on Jul. 17, 1997.

(51) Int. Cl.$^7$ .................................................. G01N 33/00
(52) U.S. Cl. ........................... 436/97; 436/164; 436/166; 436/174; 436/175; 422/61
(58) Field of Search ................. 436/12, 97, 164, 436/166, 174, 175; 422/61; 252/408.1

(56) References Cited

U.S. PATENT DOCUMENTS

| 3,652,222 | 3/1972 | Denney et al. ........................ 436/97 |
| 4,078,892 | 3/1978 | Steinrink, Jr. ........................... 436/97 |
| 5,149,272 | * 9/1992 | Wu et al. ................................ 436/97 |
| 5,183,762 | 2/1993 | Meiattini ................................. 436/97 |
| 5,872,009 | * 2/1999 | Kojima et al. .......................... 436/97 |

FOREIGN PATENT DOCUMENTS

| WO95/00843 | 1/1995 | (WO) . |
| WO96/17251 | 6/1996 | (WO) . |

* cited by examiner

*Primary Examiner*—Maureen M. Wallenhorst
(74) *Attorney, Agent, or Firm*—Brinks Hofer Gilson & Lione

(57) ABSTRACT

Methods for assay of both total bilirubin and direct bilirubin in a sample. The inventive methods enable the amounts of total and direct (conjugated) bilirubin to be colorimetrically measured in about 5 minutes, and do not require the precipitation and removal of potentially interfering substances such as proteins prior to analysis. Novel stable reagents that solubilize the bilirubin and interfering substances are also provided. A novel total bilirubin reagent causes the oxidation of the total bilirubin in the sample, and the formation of a light-absorbing bilirubin chromophore detectable in the near-infrared region of the spectrum. A novel direct bilirubin reagent causes the oxidation of the direct bilirubin in the sample, and the formation of a light-absorbing bilirubin chromophore detectable in the near-infrared region of the spectrum, whereas the chromophore formed by the unconjugated bilirubin is substantially colorless.

47 Claims, No Drawings

ASSAY FOR TOTAL AND DIRECT BILIRUBIN

This application is a 371 of PCT/US98/14779, filed on Jul. 16, 1998, which claims benefit of provisional application Ser. No. 60/052,844, filed on Jul. 17, 1997.

BACKGROUND OF THE INVENTION

The present invention is concerned with methods for the quantitative chemical analysis of bodily fluids for total billrubin and direct reacting bilirubin content, and reagents for use in the methods.

Bilirubin is an orange-colored or yellowish substance found in bodily fluids such as blood serum, plasma and amniotic fluid. It is formed as a product of the catabolism of hemoglobin. Bilirubin is transported througout the body in blood serum attached to serum albumin. Bilirubin is conjugated with glucuronic acid in the liver to form the diglucuronide. In its water soluble conjugated glucuronide form, bilirubin enters the biliary system for excretion in the bile.

There are two forms of bilirubin found in blood, namely conjugated bilirubin and unconjugated bilirubin. Conjugated bilirubin is water soluble, whereas unconijuated biliribin is non-water soluble. "Total bilirubin" refers to the total amount of both conjugated and unconjugated bilirubin in a sample. "Direct bilirubin" or "direct reacting bilirubin" refers to the amount of conjugated bilirubin in a sample.

Generally, in healthy individuals, only low levels of bilirubin are present in bodily fluids. The nonrmal range of total bilirubin in healthy adults is about 0.2–1.0 mg/dL, with about 0.0–0.2 mg/dL conjugated bilirubin and the rest unconjugated bilirubin. Elevated serum bilirubin levels are observed in a variety of disease conditions including hernolytic disorders, biliary obstruction, cholestasis, hepatitis, cirrhosis and decreased conjugation. A condition known as bilirubinemnia is frequently a direct result of these disturbances. The quantification of amount and type of bilirubini in blood serum or plasmna is useful in diagnosing these conditions, and, following diagnosis, in monitoring treatment of the disease.

All newborns have serum unconjugated bilirubin levels greater than the normal levels found in the healthy adult population, and about 50% of newborn babies are clinically jaundiced during the first 5 days of life. In the normal full-term neonate, unconjutgated bilirubin values rise to 4 to 5 mg/dL (68–85 µmol/L), and in a small percentage of newborns, these levels may rise to as high as 10 mg/dL (170 µmol/L) 48 hours after birth, with a decrease to normal values in about 7 to 10 days. This temporary increase is caused by increased bilirubin production as a result of hemolysis of erythrocytes, and by incomplete bilirubin metabolism and excretion. In about 5% of neonates, unconjugated bilirubin values of greater than 15 mg/dL (256 µmol/L) are seen. The increased production of bilirubin that accompanies the premature breakdown of erythrocytes and ineffective erythropoiesis results in hyperbilirubinemia in the absence of any liver abnormality.

The inherited disorders known as Gilbert's and Crigler-Najjar syndrome are known causes of hyperbilirubinemia. Since bilirubin cannot be conjugated at the normal rate in patients with these disorders, the rate of excretion of bilirubin is significantly reduced, and the serum concentration of unconjugated bilirubin increases. Serum total bilirubin concentrations of 20 to 50 mg/dL (342 to 855 µmol/L) are commonly seen in patients afflicted with Crigler-Najjar syndrome Type I. Patients with this disease may the in infancy owing to the development of kernicterus (bilirubin staining of the basal ganglia of the brain). In patients with Crigler-Najjar syndrome Type II, total bilirubin concentration is less than 20 mg/dL (342 µmol/L). Total bilirubin concentrations of less than 3 mg/dL (51 µmol/L) are usual in individuals with Gilbert's syndrome.

In addition, in liepatobiliary diseases of various causes, bilirubin uptake, storage, and excretion are impaired to varying degrees. Both conjutated and unconjugated bilirubin are retained in these disorders, and a wide range of abnormal serum concentrations of each form of biliubin may be observed. When any portion of the biliary tree becomes blocked or subnormally permeable, biliary passage of bilirubin and of all other constituents of bile is retarded. Thus, these substances are retained. As a result, plasma concentrations of conjugated bilirubin increase to abnormal values.

Total bilirubin assay must measure both the water soluble conjugated and the non-water soluble unconjugated bilirubin. Direct reacting bilirubin measurement is targeted to principally measure conjugated bilirubin. Thus, when total bilirubin and direct reacting bilirubin are measured, the relative amount of uncon jugated bilirubin is readily indicated by subtracting the direct reacting biliubin from the total bilirubin.

In many cases it is very important to distinguish between conjugated (direct) bilirubin and unconjugated bilirubin because the diagnostic implications of each are different. For example, in Rh disease of newborns, it is known that levels of about 20 mg/dL of unconjugated bilirubin in serum places the infant at risk of death or permanent brain damage due to the development of kernicterus. Treatment for high unconjugated bilirubin levels involve exchange blood transfusions which may themselves be life threatening and may place the infant at risk of contracting AIDS or other viral diseases. However, similar levels of conjugated bilirubin may be tolerated by the infant with no lasting effects. It is therefore important to be able to distinguish the type of bilirubin for both diagnosis and treatment.

Most bilirubin assays have been based on the diazo reaction reported by Ehrlich in 1883. A later diazo method for total bilirubin assay originally was reported by Jendrassik and Grof in 1938, and later modified by Doumas et al. in 1973. This modified Jendrassik and Grof method may be considered as the reference method by which new methods are compared. This method employs an azosulfanilic acid prepared by combining sodium nitrite with sulfanilic acid. Direct reacting bilirubin assays have used diazo reactions of various types under acid conditions in order to achieve relative specificity for conjugated bilirubin in the presence of unconjugated bilirubin. Under these reaction conditions, most of the "direct bilirubin" detected in the reaction is conjugated bilirubin. Although some of the color may be due to unconjugated bilirubin, the small amount of unconjugated bilirubin does not significantly reduce the diagnostic value of the test for detecting direct bilirubin.

Since most total and direct bilirubin assays are performed in clinical laboratories losing automated biochemical analyzers, the modified Jendrassik and Grof method is not widely used for these assays due to its poor suitability for automation. For example, the modified Jendrassik and Grof method requires the use of as many as four separate reagents while the most commonly used analyzers are designed to use only two reagents. Additionally, the azosulfanilic acid reagent used in the Jendrassik and Grof method is stable for only about one day and must be prepared regularly by the laboratory. Further, the ascorbic acid utilized in the reaction is unstable and must be prepared as often as daily.

Attempts have been made to improve the Jendrassik and Grof method. In U.S. Pat. No. 3,569,721, Denney et al. attempted to improve the Jendrassik and Grof method by replacing the ascorbic acid constituent with stable hydroxylamnine salts. Although this method avoided the use of the unstable ascorbic acid, it was still necessary to use the unstable azostilfanilic acid reagent. The method also required the use of four separate reagents. Thus, this method was unsuitable for most currently used clinical laboratory automated analyzers.

A number of other modifications of the diazo reaction have been made to simplify the reaction for automated use. Most of these attempts have used fast diazonium salts, such as 2,4-dichlorophenyl or 2,5-dichlorophieniyl diazonium salts as diazo reagents, such as the methods described in U.S. Pat. Nos. 3,754,862 and 3,754,862. However, R. Poon. et al, *Clin. Chem.* 31, 92–94, 1985, describe severe interference in this type of diazo method due to the presence of indican in the serum of patients with renal failure. The interference from indican invalidates the results of the bilirubin test using these prior art methods for the analysis of the serum of such patients. This represents a serious problem in the use of these methods.

The total bilirubin level in bodily fluids of infants has been measured by direct spectrophotometric estimation at 454 nm with correction at 540 nm However, this method cannot be applied to older children or adults due to the presence of carotene and other pigments in the serum. See, Tietz, N., *Textbook of Clinical Chemistry*, W.B. Saunders Company, (198(p. 1386. A device enmbo(lying direct spectrophotometric observation has been described in Goldberg, U.S. Pat. No. 3,569,721.

The specificity of the measuremnent of adult bilirubin by direct spectrophotometric observation has been improved by making observations before and after the destriction of bilirubin with the enzyme bilirubin oxidase. Although the enzyme treatment improves specificity, the enzyme reagents are unstable and do not solve the stability problems of the diazo methods. Additionally, enzymes are costly, relative to diazo reagents.

In *Ann. Clin. Biochem.*, 30:175–179, (1993), O'Leary et al described a two-step method based upon the measurement of the absorbance of bilirubin itself at about 480 nm, followed by measurement of the absorbance at 480 nm after destruction of the bilirubin with ferricyanide. The reaction was carried out at neutral pH conditions. Although the O'Leary methods, represented an improvement in accuracy and stability in comparison to diazo methods, the method is limited due to the use of the 460–480 nm wavelengths for detection. At these wavelengths, highly lipemic or hemolyzed sera may cause the absorbance of the sample plus bilirubin to exceed the detection capability of automated systems, and therefore, a false result may be produced. Additionally, proper mixing of the first reagent with the serum is critical prior to the measurement of the absorbance at 480 nm in the first step. Automated devices do not always provide the ability to mix a first reagent and serum prior to the addition of a second reagent. When the method is applied to such systems, the precision is not satisfactory for clinical use.

In 1964 Ferro and Ham (U.S. Pat. No. 3,348,920), taught that total bilirubin could be quantified by reacting the bilirubin in a supernatant solution under acid conditions and in the presence of ferric ion. Prior to this reaction, the protein in the sample is precipitated and removed from the solution. This method requires multiple steps and a total time of tip to thirty minutes. The time and the multiple steps required in this method are incompatible with the types of automated analyzers commonly used in clinical laboratories, in particular, due to the necessity of performing filtration or centrifugation for separation of the precipitate. Additionally, the reactants in the Ferro/Ham method include highl levels of iron. Iron is a potential contaminant that may adversely affect the results of other assays, such as serum iron, that are frequently performed on the same automated equipment. Ferro and Ham did not teach a method for direct bilirubin assay, as the method detects only total (both unconjugated and conjugated) bilirubin.

Serious errors in most, if not all, commonly used total and direct bilirubin assays are caused by the presence of lipemia (fatty substances) and hemolysis (red blood cell contents) in the sample to be assayed. Glick has reported that a significant percentage of blood samples presented to clinical laboratories for assay contain these interferences. M. Glick, *Interferographs: User's Guide to Interferences in Clinical Chemistry Instruments*, Second Edition, 1991, Science Enterprises, Inc. Indianapolis, Ind. Glick et al. have reviewed the performance of most commonly used clinical chemistry automation in the presence of lipemia and hemolysis in the sample. Melvin R. Glick and Kenneth W. Ryder, *Clinical Chemistry* 33 pages 1453–1458, 1987. The work of Glick indicates that bilirubin assays are among the most prone to interference from lipemia and hemolysis of all commonly performed diagnostic assays.

Thus, prior art automated methods continue to be subject to serious errors. In addition, the reagents used in such prior art methods often have limited stability. Accordingly, it is desired to provide a method for assay of total and direct reacting bilirubin in both adult and infant bodily fluid samples that overcomes the problems and limitations encountered with prior art methods, and that utilizes reagents that are suitable for use with automated laboratory analyzers.

SUMMARY OF THE INVENTION

The present invention overcomes the problems of the prior art methods by providing automated methods for the assay of total bilirubin and direct reacting bilirubin in bodily fluids. Thle inventive methods enable the amounts of both total bilirubin and direct reacting bilirubin in a sample to be colorimetrically measured in about five minutes, and do not require separation of potentially interfering substances by techniques such as centrifugation or filtration prior to the analysis.

The present invention further provides novel reagents for use in the methods. Specifically, a stable reagent is provided which can be added to a sample of bodily fluid to colorimetrically quantify the total bilirubin content thereof as a single step without prior protein precipitation and removal. Similarly, a stable reagent is provided which can be added to bodily fluid to colorimetrically quantify the direct bilirubin content thereof without protein precipitation and removal.

DETAILED DESCRIPTION OF THE INVENTION

It has now been found that certain reagents or reagent mixtures are effective for the solubilization of both bilirubin and proteins in bodily fluids, and for the oxidation of the bilirubin in the sample to form a near-infrared light-absorbing chromophore. The oxidation of bilirubin to form the chromophore can take place while protein is present.

This contrasts with the teachings of the prior art that protein must be precipitated and separated from the bilirubin-containinig supernatant liquid prior to reacting the bilirubin for analysis. These reagents may be advantageously utilized in novel automated methods for the assay of total bilirubin and direct reacting bilirubin.

Total Bilirubin Assay

A preferred reagent for use in the assay of total bilirubin comprises the following constituents: (a) a solvent for the bodily fluid in which the bilirubin and the proteins are soluble; (b) an acid; and (c) a promoter for speeding up the oxidation of the bilirubin and the formation of a chromophore which is detectable in the near-infrared region of the spectrum.

Dimethyl sulfoxide (DMSO) is the preferred solvent, either alone or in combination with other protein miscible solvents. Other solvents, such as dimethyl formanide (DMF), ethylene glycol, a variety of ethylene glycol ethers such as ethylene glycol monometlhyl ether and polyethylene glycol, lower alkyl alcohols such as methyl and ethyl alcohol, and other related protein miscibile organic solvents are also acceptable, preferably for use in combination with DMSO. However, these organic solvents can be used alone, in combination with each other, or in combination with water and detergents. The principal important characteristics of an acceptable solvent for total bilirubin assay is that the proteins must stay in solution in e solvent, and that all bilirubin, i.e., conjugated and unconjugated, must be solubilized. The use of some solvents alone, such as DMF, may be problematical in some commercial uses since they may affect the transparency of plastic cuvettes of the type that are presently used in some automated systems. DMF may also cause protein turbidity if present in too high a concentration. Proper use of blanking and standard samples should enable one of skill in the art to select a suitable solvent without undue experimentation, when utilizing the teachings of this invention.

When DMSO is employed as the protein and bilirubin solvent in a total bilirubin assay using automated laboratory equipment of the type that refrigerates all reagents, the DMSO is preferably diluted with approximately 10% water, or alternatively, 10% water containing about 5% detergent. This dilution prevents the DMSO from solidifying at low temperature. It was found that the absorbance of serum lipids progressively diminishes as the concentration of DMSO approached 100% of the non-acid constituent of the solvent mixture. At 100% DMSO in the non-acid constituent of the mixture, the absorbance of serum lipid turbidity was negligible, thereby eliminating interference from lipemia. Thus, in low temperature storage applications, it is preferable to have the DMSO concentration as high as possible, while at the same time diluting this solvent with a small amount of water, or water/detergent mixture, to prevent solidification of the DMSO.

Water containing detergent is also useful as a protein and bilirubin dissolving solvent. However with this water/detergent solvent, the chromophore sensitivity is not as great as when DMSO is used. When water containing detergent solvent is used, the absorbance of the chromophore peaks at about 650 nm instead of about 700 nm when principally DMSO is used. In addition, the water and detergent solution may not be as effective as DMSO in clearing serum lipids and thereby preventing their interference in the assay.

Many acid soluble ionic detergents and non-ionic detergents are known in the art to promote the reactivity of bilirubin in diazo reactions. Examples of such detergents are provided in an article by Perlman and Lee, *Clinical Chemistry*, 20, 447–453, (1974), the disclosure of which is incorporated herein by reference. These detergents were found to be useful when aqueous solvent mixtures were used in the present invention. Preferably, at least one nonionic and/or zwitterionic detergent may be used. Nonionic detergents such as polyoxyetlhylene 23 lauryl ether (available from Sigma-Aldrichi, St. Louis, Mo. under the trademark BRIJ-35) and octoxynol-9 and octoxynol-10 (available from Sigma-Aldrich under the trademark TRITON X-100), and zwitterionic detergents such as cocoamidopropyl-N,N-dimethyl-N-2-Hydroxypropylsulfobetaine (sold tinder the trademark LONZAINE CS), or mixtures of the foregoing, are preferred detergents.

Weakly anionic detergents (i.e., having a carboxyl group) should not be used because they are poorly soluble at the pH of the reagent. Strongly anionic detergents are undesirable with reagents containing copper or iron as promoter due to possible precipitation. Cationic detergents are undesirable because of the tendency to co-precipitate with anionic compounds in blood serum.

Many acids may be utilized in the reagent for measurement of total bilirubin. These acids include strong mineral acids, such as hydrochloric acid, nitric acid and sulfuric acid, strong organic acids, such as methanesulfonic acid, and weak organic acids, such as acetic acid, sticcinic acid, oxalic acid, maleic acid and glycolic acid, either alone or in combination with other acids. Although the following concentrations are not necessarily the only concentrations of the subject acids that may be employed, these concentrations are believed to be optimal for use in the inventive method for total bilirubin assay: about 0.05–0.1 normal for strong acids such as hydrochloric, nitric and sulfuric acids, 0.3–1.0 normal for organic acids such as methanesulfonic acid, and 10–20% (v/v) for weak organic acids.

Generally, it has been found that the use of strong mineral acids in the concentrations described above enables the formation of a chromophore having greater absorbance and in a shorter time when compared to the use of the organic acids. Similarly, the use of stronger organic acids enables the formation of the chromophore having greater absorbance and in a shorter time than the use of weaker organic acids. When weak acids are used, it is generally necessary to increase the concentration of the promoter, as further described below. Furthermore, when weak organic acids are used, the peak wavelength shifts to about 650 nm, when compared to about 700–710 nm with the strong mineral acid. Since turbidity has less effect at the higher wavelength, the use of the mineral acid generally provides optimal results. When increased turbidity is present, it is generally necessary to include a dynamic sample blank or bichromatic correction to minimize the effect of the turbidity. When using a dynamic blank (which does not include a promoter), the incubation time and the blank reagent should be kept as short as practical to minimize spontaneous chromophore formation in the absence of the promoter.

Although the optimum concentration of the strong acids have been provided above, higher concentrations of strong acids can be used in certain applications. However, when higher concentrations are used, the effect of protein turbidity is normally increased. Therefore, automated means for correcting for this increased turbidity, such as those described in the preceding paragraph, should normally be used.

It has been discovered that certain substances (i.e. "promoters"), if used in narrow concentration limits, are capable of promoting chromophore formation from both unconjugated and conjugated bilirubin within about a five minute time period. In addition, if hemoglobin is present in the sample due to such conditions as hemolysis or blood substitute administration, the hemoglobin was found to contribute little color at the wavelengths used for detection of the chromophore formed from bilirubin.

One such promoter found to be useful is nitrite ion, which may preferably be added to the reagent as sodium or potassium nitrite. Although sodium nitrite is known to be unstable in even weak acids, the nitrite ion was found to be sufficiently stable to promote the formation of the chromophore from conjugated and unconjugated bilirubin after incubation at 37° C. for one week. This stability indicates a refrigerated stability at 4° C. for one year. It was discovered that small amounts of nitrite, on the order of 50 to 100 μmolar nitrite, were effective promoters of chromophlore formation from both conjugated and unconjugated bilirubin in bodily fluids such as serum or plasma. Excessive amounts of nitrite were found to cause instability of the color produced. This instability is believed to be due to oxidation of the chromophore by nitrite to form non-near-infrared absorbing substances.

Another promoter found to be useful is ferricyanide ion, which may preferably be added to the reagent as potassium or sodium ferricyanide. Ferricyanide ion, when used in small amounts, greatly increases the rate of the reaction without producing an unstable color. Ferricyanide concentrations of about 2–5 millimole per liter were found to promote chromophore formation. Although potassium fenicyanide has been reported to decompose in acid solution, the ferricyanide ion was found to be sufficiently stable in the prepared reagents of the present invention to promote the formation of chromophore from both conjugated and unconjugated bilirubin after incubation at 37° C. for one week, indicating a refrigerated stability at 40° C. for one year.

Another promoter which was found to be useful was cupric ion, which may be conveniently added as cupric sulfate, either with or without approximately equimolar concentrations of potassium iodide. The cupric-iodide promoter was effective in concentrations of about 1–2 millimoles per liter.

Other promoters that may be useful in promoting chromophore formation from both conjugated and unconjugated bilirubin in the solvent mixture used for total bilirubin were compounds ranging in oxidizing potential, expressed as single electrode potentials (E°, volts), from about 1.00 to 0.34 volts. In addition, it was found that such compounds could be advantageously mixed together to achieve desirable effects in terms of reaction rates, color stability and stability of reagent. In general, promoters having high E° values, such as nitrite, are most likely to adversely affect color stability. Smaller amounts of these substances can be used with promoters having low E°, such as cupric ion, to improve color stability. There also exists somewhat of an inverse relationship between the acid level and the concentration of the promoter required. Very little amounts of promoter can be used when using high levels of acid, however, as stated, there are undesirable turbidity effects from using such high acid levels.

Unlike the prior art Ferro and Ham teaching, it is normally not preferred to use iron in the protein dissolving solvent of the present invention. Hemoglobin, if present, forms a green near-infrared absorbing compound in the presence of iron. This green-colored compound causes errors in the measurement of the bilirubin. Since hemoglobin is a protein, it is precipitated in the prior art method, and thereby separated from the remaining reactants. It was further discovered that chromophore formation from unconjugated bilirubin proceeds very slowly when ferric ion alone is used as an oxidant, and that high concentrations of ferric ion are required. Even when ferric ion concentrations as high as 4,000 moles per liter are used, the reaction does not reach completion within five minutes as required for optimnal automation. High concentrations of iron in reagents are also often undesirable when used with automated systemns since other important diagnostic tests performed on the same automation may be adversely affected by residual iron which may be carried over from a prior test.

Generally speaking, smaller amounts of promoters having E° values near 1 volt are desired when compared to promoters having lower E° values. High concentrations of promoters having E° values near 1 volt are undesirable because they may cause the chromophore to fade. High concentrations of compounds with lower E° values are desired, and wider concentration variances can be tolerated without risk of the chromophore fading. Thus, for example, a small amount of a compound having a micromolar concentration of about 25 μmoles/liter and an E° of about 1 volt can be combined with a higher amount of a compound having a concentration of about 5–10 millimole/liter and an E° of about 0.34 volts. The compound having the higher E° value is believed to particularly accelerate the formation of near-infrared absorbing chromophore from unconjugated bilirubin, while the compound having the lower E° value is believed to produce greater color and reagent stability.

Additionally, the use of the compounds having the highest E° value alone, in the small molar concentrations required to avoid color fading, may be undesirable when assaying sera containing high levels of endogenous reducing substances, such as glutathionie and ascorbic acid, which may be present in the serum or plasma sample in high aggregate molar concentrations. The additional inclusion of a higher molar concentration of the lower E° value compound enables the endogenous serum reducing substances to be oxidized. Otherwise, the reducing substances may reduce some or all of the promoter and thereby change the dynamic measuring range in the case of diminished promoter level or eliminate the detection in the case of the elimination of the promoter.

The following chart illustrates the E° volts of oxidizing potential and the approximate optimal molar concentration of some of the promoters of oxidation found to be useful in the present invention for total bilirubin in serum or plasma:

| PROMOTER ions and (additive) | E°, volts | Concentration μmoles per Liter |
|---|---|---|
| Nitrite (as Sodium Nitrite) | 1.00 | 50 |
| Cupric + Iodide (as cupric sulfate and potassium iodide) | 0.86 | 1,500 |
| Ferric (as ferric chloride) | 0.771 | >5,000 |
| Ferricyanide (as potassium ferricyanide) | 0.36 | 2,000 |
| Cupric | 0.34 | 2,000 |

EXAMPLES OF REAGENTS FOR USE IN TOTAL BILIRUBIN ASSAY

The following example describes a reagent including more than one promoter: 25 μmoles of nitrite ion, added as sodium nitrite, is combined with either 200 μmoles of ferricyanide ion, added as potassium ferricyanide, or 100

μmoles of cupric ion, added as cupric sulfate pentahydrate, in a liter of solvent containing 25 milliliters of concentrated hydrochloric acid, 100 ml of water with thle remainder being DMSO. A lower concentration (relative to the amount when used alone) of the substances with the higher E° volts of oxidizing potential can be used in combination with lower concentrations (relative to the concentration required when used alone) of low E° volts of oxidizing potential substances to practice the invention. This discovery was unexpected because it is not predictable from the E° volts of oxidizing potential of substances used alone.

Listed below are several examples of preferred reagent formulations for total bilirubin assay. The reagent may comprise a single reagent component, or alternatively, may be provided as a two-component formulation. Normally, single reagents are preferred, because they are generally more convenient to use and are more economcal. However, two-component reagent formulations are preferably used with certain promoters, primarily due to the instability of some promoters in acid, and when a dynamic blank correction is to be used. In two-component formulations with an unstable promoter, the component containing the promoter is separate from the component containing the acid. Of the promoters listed hereinabove, only ferricyanide is considered unstable in acid. However, if the present invention is carried out using promoters other than those specifically listed herein, the promoter should be tested to determine its stability in acid. If found to be unstable, then a two-component formulation should be utilized.

The reagent described below is stable as a single reagent. The use of a single reagent is generally more efficient and simple for the user when practicing the invention. The user does not need to combine reagents prior to use, and there is normally greater reagent stability, thereby potentially avoiding waste. Cupric ion is the presently preferred promoter in the single reagent formulations, although other promoters generally work at least as well.

As stated, higher than optimal acid concentrations may cause precipitation or turbidity due to some serum proteins. The effect is slight at higher bilirubin levels but may cause an intercept problem in comparison to the traditional diazo method, thereby resulting in lower bilirubin values being falsely measured too high. Accordingly, in the preferred embodiments for total bilirubin assay, cupric ion is used as the promoter in a solvent having an acid concentration of 0.06 N. Lower concentrations may cause the reaction to be too slow, while higher concentrations may cause the intercept error.

The preferred reagent for total bilirubin assay therefore includes the following ingredients per liter:

| Ingredient | Amount |
|---|---|
| Concentrated hydrochloric acid | 5 ml |
| Water | 95 ml |
| DMSO | 900 ml |
| CuSO4.5H2O | 0.37 gm |

In order to prepare this reagent, the HCl and the CuSO4.5H2O are mixed with the water, and the CuSO4 is allowed to dissolve. The DMSO is then added in an amount to make a final formulation of 1 liter. The approximate concentrations of the ingredients in the final formulation are about 90% DMSO, 0.06 N HCl, and 1.5 mM Cu. This mixture was stable after incubation at 37° C. for three months, thereby indicating a stability of at least one year at 25° C. (room temperature). Incubation at elevated temperatures is a known way of accelerating stability testing. For further information, see work done by Nicolas Lordi and Morton Scott, "Stability Charts: Design and Application to accelerated Testing of Pharmaceuticals", *Journal of Pharmacelitical Sciences*, Volume 54, 531–537 (1965), the disclosure of which is incorporated herein by reference.

Another preferred reagent for total bilirubin assay includes the following ingredients:

| Ingredient | Amount |
|---|---|
| H2O + NaCl | 15 ml H2O + 0.135 gm NaCl |
| Concentrated HCl | 5 ml |
| CuSO4.5H2O | 0.37 gm |
| DMSO | 590 ml |
| Ethylene glycol | 395 ml |

In order to prepare this reagent, the water and sodium chloride, acid, and copper sulfate are mixed together and dissolved. Then, the DMSO and ethylene glycol are added, such that the final volume is one liter. The approximate final concentrations of the ingredients are: 2.3 mM NaCl, 1.5 nmM Cu, 0.06 N HCl, 59% DMSO and 40% ethylene glycol. This mixture was stable after incubation at 37° C. for seven days, thereby indicating a stability of at least one year under refrigeration at 4° C.

NaCl may improve the stability of the certain abnormal proteins that have low solubility in acids. Increasing the salt concentration is a known way to keep such abnormally-soluble proteins in solution. The use of ethylene glycol (and DMF in the next example) shows that organic solvents other than DMSO may also be utilized. Although DMSO is the preferred solvent, at times it may preferable to use other less expensive or more readily available solvents, generally in combination with DMSO.

Another preferred reagent includes the same amount of water, NaCl, HCl and CuSO4 as the preceding example, but in this case the solvent comprises a mixture of 295 ml DMSO, 395 ml ethylene glycol and 295 ml DMF. This mixture was also stable after incubation at 37° C. for seven days, thereby indicating a stability of at least one year under refrigeration at 4° C. Although the use of DMF is acceptable in certain assays, it is not normally favored as it may cause protein turbidity if present in too high a concentration.

An example of a reagent that may be utilized in the method for total bilirubin assay with a weak acid includes the following ingredients:

| Ingredient | Amount |
|---|---|
| H2O | 4 ml |
| Acetic acid | 100 ml |
| CuSO4.5H2O | 0.75 gm |
| DMSO | 896 ml |

In this case, the approximate final concentrations of the ingredients are: 3 mM Cu., 10% acetic acid and 90% DMSO. Higher concentrations of acid may be used, however such higher concentrations are normally undesirable due to potential corrosion of laboratory equipment and increased risk to laboratory workers.

A 2-component working reagent for total bilirubin is described below:

Component I

| Ingredient | Amount |
|---|---|
| Concentrated HCl | 10 ml |
| Water | 90 ml |
| DMSO | 900 ml |

These ingredients are mixed to form component I. Component I was stable after incubation at 37° C. for seven days, thereby indicating a stability of at least one year under refrigeration at 4° C.

Component II

| Ingredient | Amount |
|---|---|
| Potassium ferricyanide | 2.91 grams |
| Deionized water | 100 ml |
| DMSO | 900 ml |

These ingredients are mixed to form component II, which does not include an acid. This mixture was also stable after incubation at 37° C. for seven days protected from light in a brown bottle, thereby indicating a stability of at least one year under refrigeration at 4° C.

To form the working reagent for use in the inventive method, twenty ml of Component I are mixed with eight ml of Component II. This mixture is stable for at least one month at ambient temperature protected from light.

Method for Total Bilirubin Assay

Twenty $\mu$L of a sample of bodily fluid is mixed with 200 $\mu$L of working reagent and incubated for 4–8 minutes at 37° C. The absorbance of the mixture is measured with a spectrophotometer at a selected wavelength between 650–710 nm. The absorbance of a reagent blank prepared by substituting water for the sample is similarly measured. Preferably, these absorbance measurements are made at an optimal wavelength between 700–710 nm, and most preferably, at 700 nm. The net absorbance is determined by subtracting the reagent blank absorbance from the test absorbance. The results are calculated by comparing the absorbance (net of reagent blank reading) of the unknown sample to the absorbance (net of reagent blank reading) of a similarly-treated standard of known total bilirubin concentration by the following equation:

Concentration of Unknown =

$$\frac{A_{test\ sample} - A_{reagent\ blank}}{A_{test\ standard} - A_{reagent\ blank}} \times \text{Concentration of the standard.}$$

When increased turbidity is present in the sample, due to the presence of substances such as lipemia, bichromatic correction or a dynamic sample blank should be utilized to minimize the effect of the turbidity. If a wavelength in the range of 740–800 nm is available on the automated spectrophotometer being used, a secondary reading should be taken at this wavelength. Other wavelengths may be used for the secondary reading as long as the absorbance due to turbidity at the secondary wavelength remains essentially constant when compared to its absorbance at the primary wavelength. If a bichromatic correction is to be utilized, absorbances of the test sample, reagent blank and test standard are taken at a primary wavelength ($1°\lambda$), and then at a secondary wavelength ($2°\lambda$). Bichromatic measurement corrects for errors due to turbidity because absorbances due to turbidity remain relatively constant for the primary and secondary wavelengths, while absorbances of the chromogen decreases substantially from the primary to the secondary wavelength. Therefore, subtraction of the absorbance at the secondary wavelength from the absorbance at the primary wavelength provides the absorbance due to the bilirubin chromogen. The concentration of bilirubin is calculated according to the following equation:

Conc. of unknown =

$$\frac{(A_{tst\ sample1°\lambda} - A_{rgt\ blk1°\lambda}) - (A_{tst\ sample2°\lambda} - A_{rgt\ blk2°\lambda})}{(A_{tst\ std1°\lambda} - A_{rgt\ blk1°\lambda}) - (A_{tst\ std2°\lambda} - A_{rgt\ blk2°\lambda})} \times \text{conc. of std.}$$

If the chemical analyzer does not permit bichromatic correction, a dynamic blank procedure may be used. The dynamic blank procedure is used with 2-component reagents. The first component includes solvent and acid, but without the promoter. The second component includes solvent and promoter. If the promoter is stable in acid, the second component may also include an acid. 20 $\mu$L of sample is added to 200 $\mu$L of the first component, and the absorbance $A_{test1}$ is measured at a selected wavelength between 650–710, within 1–2 minutes. This reading consists primarily of the absorbance from interferences in the sample. Then, 80 $\mu$L of the second component is added, and the absorbance $A_{test2}$ is measured at the same wavelength after 4–8 minutes. Similarly, an aqueous protein-based bilirubin standard is added to the first component in the same manner as the sample, and the absorbance $A_{std1}$ is measured after 1–2 minutes at the same wavelength. The small amount of the second component is similarly added, and the absorbance $A_{std2}$ is measured after 4–8 minutes.

Since the respective volumes of the solutions that are subjected to the second absorbance readings are greater than the volumes of the solution that are subjected to the first absorbance readings (due to the dilution effect caused by the addition of the second component), a volume correction is normally factored into the final result. Some automated analyzers provide mathematical correction for the volume factor, others do not. The volume factor is calculated according to tlhe following equation:

Volume factor =

$$\frac{\text{Volume of first cmpnt} + \text{volume of sample added}}{\text{Vol. First cmpnt} + \text{Vol. Second cmpnt} + \text{vol. sample added.}}$$

The concentration of bilirubin in the test sample is calculated according to the following equation:

$$\text{Conc. of unknown} = \frac{A_{test2} - [(A_{test1} \times \text{Vol. factor})]}{A_{std2} - [(A_{std1} \times \text{Vol. factor})]} \times \text{conc. of the std.}$$

The following parameter settings may be used with the Synermed® IR200 analyzers when using a bichromatic correction. However, one of skill in the art will be able to readily determine appropriate parameter settings and component volumes for a particular assay when utilizing the teachings of the present invention.

| Test Name: | Total Bilirubin: |
|---|---|
| Sample Volume: | 30 μL |
| Reagent Volume: | 220 μL |
| Blank: | Reagent |
| Incubate: | 240 seconds |
| Wavelength: | 700 nm |
| 2$^{nd}$ Wavelength: | 740 nm |
| Correction: | 0.7000 |

Direct Reacting Bilirubin Assay

A further aspect of the present invention is the discovery that conjugated bilirubin ("direct reacting" or "direct" bilirubin) can be quantified by an automated method even in the presence of high levels of unconjugated bilirubin. Upon quantifying both the conjugated (direct) bilirubin, and the total bilirubin, as described above, the amount of unconjugated bilirubin can be quantified by a simple calculation, as it represents the difference between these assayed amounts.

The novel reagent for the detection of direct reacting bilirubin is comprised of at least the following components: (a) an aqueous component containing an acid for dissolving both the serum or plasma proteins, and the conjugated bilirubin of the sample; and (b) an oxidant for promoting the oxidation of conjugated bilirubin while promoting very little oxidation of unconjugated bilirubin. To optimally practice the invention for direct bilirubin, a solvent such as a DMSO/water mixture is also included in the reagent. In addition to the foregoing, it is preferred to include one or more surfactants such as TRITON X-100 with or without BRIJ-35 (obtained as a 30% in water solution).

The novel reagent causes the formation of a near-infrared absorbing chromophore from conjugated bilirubin. Unconjugated bilirubin fornms chromophores having relatively little color in the reagent in the short time used for the measurement. The method optimally requires a critically short incubation time of 3–7 minutes prior to detecting the chromophore.

Strong mineral acids such as hydrochloric acid, nitric acid and sulfuric acid having concentrations from 0.06 to 0.6 N are preferred in the aqueous component. Although other acids such as acetic acid or glycolic acid will also promote the formation of color from conjugated bilirubin, they are not normally desirable for use in the direct bilirubin reaction. These acids tend to make the unconjugated bilirubin more reactive, thereby decreasing the specificity of the direct bilirubin assay for conjugated bilirubin.

Only sufficient acid to optimize the sensitivity of the reaction need be used. Additional acid normally increases the corrosiveness of the reagent and does not appreciably improve the desirable characteristics of the reagent. Additionally, certain abnormal serum proteins, if present in the sample, are more likely to precipitate at higher acid concentrations. It was found that 0.07 N HCl produced optimal sensitivity when using ferric ion as a promoter, 0.1 N HCl produced optimal sensitivity when using ferricyanide as a promoter, and as high as about 0.5 N HCl provided optimnal sensitivity when using cupric ion as a promoter. However, for best results it is preferred that an HCl concentration of no greater than 0.25 N be used with cupric ion to avoid protein turbidity. In general, increasing the acid concentration increases the sensitivity of the reaction for direct bilirubin. However, high amounts of certain acids, such as 0.25 N HCl, are sometimes undesirable because of the corrosive effects of stronger acids on the automated device. Using the teachings of the present invention, the skilled artisan can optimize these amount of an particular acid required to optimize sensitivity and at the same time avoid corrosiveness and protein turbidity without undue experimentation.

Although the use of a strong mineral acid in the range stated above is considered optimal, the use of organic acids, such as about 35% acetic acid, may also be used. If organic acids are used, these acids are preferably combined with an organic solvent, such as DMSO, DMF, ethylene glycol and ethylene glycol ethers. The combination of these acids with an organic solvent is preferred because it increases the intensity of the color formed. However, if organic solvents are used in concentration greater than about 50% of the overall volume of the reagent, the specificity of conjugated bilirubin in the presence of unconjugated bilirubin will decrease. This specificity loss is particularly acute when a weak organic acid is used in combination with excess amnounts of an organic solvent. In general, with reagents utilizing weak organic acids, the sensitivity is reduced when compared to the use of strong mineral acids. Also, the peak wavelength is undesirably shifted to about 650 nm, from the preferred range of about 700–710 nm.

The specific oxidation promoter selected should have a low single electrode potential, $E°$, i.e., between about 0.34 and 0.78 $E°$. Cupric ion, ferric ion and ferricyanide are the preferred promoters. Ferricyanide ion, preferably added as sodium or potassium ferricyanide, is an effective oxidation promoter in a concentration of about 0.3 to 3 millimoles per liter. A preferred concentration is 1.5 millimoles per liter. At this concentration, the promoter provided adequate detection of conjugated bilirubin while minimizing the detection of unconjugated bilirubin. Similarly, cupric ion at a concentration of about 0.1 mM to 10 mM was also found to be an effective promoter. A preferred concentration of cupric ion is 3 μM. Ferric ion was found to be an effective promoter at concentration levels between about 69 μM and 555 μM. A preferred concentration is about 138 μM. At higher concentrations of iron, specificity for the detection of conjugated bilirubin in the presence of unconjugated bilirubin is diminished.

The prior art Ferro and Ham method taught that after protein removal, the ferric ion and acid oxidized the total bilirubin in serum (presumably both conjugated and unconjutgated bilirubin) to a blue or green product in thirty minutes. The method did not teach a means of measuring only the conjugated bilirubin. However, in the present invention it was found that even without protein precipitation and removal, the solvent conditions and the reaction duration could be optimized in such a way that the formation of interfering chromophores from unconjugated bilirubin could be minimized. Therefore, primarily only conjugated bilirubin react under the reaction conditions of the present invention, even in the presence of high levels of unconjugated bilirubin. The protein removal step in the prior art method is unnecessary in the inventive method.

Although high concentrations of some promoters (such as the 10 M cupric ion concentration) may be used, the specificity for conjugated bilirubin in the presence of unconjugated bilirubin progressively decreases as promoter concentration is increased. Additionally, excessively high concentrations of oxidation promoter may cause the chromophore to fade. In addition to the foregoing, it is also within the scope of the present invention to use mixtures of different oxidation promoters.

The solvent is preferably a DMSO-water mixture. In the preferred embodiment, the DMSO concentration should not be greater than about 50% (v/v) of the final volume of the reagent. The presence of about 50% DMSO in the reagent intensifies the absorbance of the chromophore, and shifts the peak absorbance from about 680 nm to about 700 nm. Since lipemia and other chromatic substances in serum have lower absorbances at the longer wavelength, the shift in absorbances minimizes interference from these substances. A further advantage is that many automatic analyzers have 700 nm wavelength available for detection, whereas fewer have the capability to measure at 680 nm.

If the DMSO concentration exceeds about 50% in the reagent, it has been found that the specificity for conjugated bilirubin in the presence of unconjugated bilirubin deteriorates. Similarly, if the DMSO concentration is much below about 50%, the sensitivity is reduced. If potassium ferricyanide is the promoter, the 50% DMSO causes a slight loss in specificity. This loss of specificity is not observed when cupric ion is used as the promoter. This result is surprising given the E° volts of oxidizing potential of the two compounds. It is believed that relative affinity for the hydrophobic unconjugated bilirubin molecule may be responsible. Copper may form an association with the carboxyl groups of the bilirubin molecule which is not believed to be the site of oxidation. Altlough the other organic solvents used with the total bilirubin reagent may also be substituted for or used in combination with DMSO in a direct bilirubin solvent, the use of DMSO in combination with deionized water is preferred because it provides optimal specificity for conjugated bilirubin in the presence of unconjugated bilirubin, and provides optimal sensitivity for the reaction.

The addition of TRITON X-100 to the working reagent improves the specificity for conjugated bilirubin in the presence of unconjugated bilirubin. When a two component reagent is used, TRITON may be added to either the first or the second component, or preferably, to both components. Each liter of working reagent normally contains about 0.5 to 1.7 ml of TRITON X-100. Amounts greater than about 1.5 ml per liter may cause some turbidity in the reagent. In addition, TRITON X-100 clarifies the lipemia in the bodily fluid sample. BRIJ-35 aids in preventing TRITON turbidity, and also assists in clarifying lipids turbidity.

When reagents prepared according to the novel concepts of the present invention are used with a sample containing both conjugated and unconjugated biliubin, the reaction time is less than seven minutes at 37° C., in order to make the reaction more specific for conjugated bilirubin. When the proper combination of short time of reaction and reagent conditions is met, the inventive method for direct reacting bilirubin compares well with the Jendrassik and Grof reference method for direct reacting bilirubin.

EXAMPLES OF REAGENTS FOR USE IN DIRECT BILIRUBIN ASSAY

Listed below are several preferred formulations for reagents for use in direct bilirubin assay.

The preferred reagent for direct bilirubin assay comprises the following components per liter of final reagent:

| Ingredient | Amount |
| --- | --- |
| Concentrated HCl | 13 ml |
| TRITON X-100 | 1.7 ml |
| Deionized water | 506 ml |
| CuSO4.5H2O | 0.74 gm |

-continued

| Ingredient | Amount |
| --- | --- |
| DMSO | 480 ml |
| BRIJ. 30% | 2.6 ml |

The ingredients are mixed together in the following order to obtain about a liter of reagent. The final reagent concentrations are approximately 48% DMSO, 0.16 N HCl, 1.7 ml/L TRITON, 2.6 ml/L BRIJ and 3 mM Cu.

Another preferred formulation for direct bilirubin assay uses 50% DMSO, and is prepared as follows:

| Ingredient | Amount |
| --- | --- |
| Concentrated HCl | 20 ml |
| TRITON X-100 | 0.75 ml |
| Deionized water | 479 ml |
| CuSO4.5H2O | 0.249 gm |
| DMSO | 500 ml |

The ingredients are mixed together to form a liter of reagent. The final reaction concentrations are 50% DMSO, 0.25 N HCl, 0.75 mil/l TRITON, and 1 mM Cu.

Single reagent formulations can be made without the organic component (DMSO), however, in this instance the copper concentration must be increased to about 10 mM to compensate for the use of the water-only matrix. An example of a single reagent formulation with a water-only matrix is provided below:

| Ingredient | Amount |
| --- | --- |
| Concentrated HCl | 20 ml |
| TRITON X-100 | 0.75 ml |
| Deionized water | 979 ml |
| CuSO4.5H2O | 2.49 gm |

The ingredients are mixed together to form a liter of reagent. The final reaction concentrations are 0.25 N HCl, 0.75 ml/l TRITON, and 10 mM Cu.

When DMSO is used, a lower amount of promoter is required than with other organic solvents. As stated, it is normally preferable to use as small amount of promoter as possible, because the use of large amounts of promoter may adversely affect the specificity of the reaction for conjugated bilirubin in the presence of unconjugated bilirubin.

Ferric ion may be substittited for cupric ion as a promoter in the formulations described above by adding FeCl3 in the amount of about 0.026 grams per liter (138 μmolar). The amount of HCl should be reduced to about 5.4 ml per liter (0.067 N). The FeCl3 should be first dissolved in the required amount of acid before adding both components to the water.

Two component reagent formulations may be prepared by formulating a first component without a promoter, and a second component with a promoter. When using cupric ion as a promoter, the first reagent contains only HCl, water, DMSO and TRITON, in similar concentrations as the single reagent. The second reagent contains HCl, water, DMSO and TRITON in the same concentrations as first component, and about 4.4 gm/L CuSO4.5H2O, which compensates for the mixing of nearly 5 parts of the first component with 1 part of the second component. In this case the promoter is stable in the acid. Having a two-component reagent allows for the use of a dynamic blank correction, which is desirable if the particular analyzer cannot perform bichromatic correction. A preferred 2-component reagent includes the following components:

| Component I | |
|---|---|
| | Amount |
| Concentrated HCl | 13 ml |
| TRITON X-100 | 1.7 ml |
| Deionized water | 506 ml |
| DMSO | 480 ml |
| BRIJ-30% | 2.6 ml |

| Component II | |
|---|---|
| Ingredient | Amount |
| Conc. HCl | 13 ml |
| TRITON X-100 | 1.7 ml |
| Deionized water | 506 ml |
| DMSO | 480 ml |
| CuSO4.5H2O | 4.4 gm |
| BRIJ-30% | 2.6 ml |

The final reaction concentrations are HCL, 0.16 N; TRITON X-100, 1.7 ml/L; copper sulfate, 3 mM/L; DMSO, 48% v/v; BRIJ-30%, 2.6 ml/L.

When using ferricyanide as a promoter, the first component contains HCl, water and TRITON, and the second component contains only TRITON, water and 1.75 gm/liter potassium ferricyanide. Ferricyanide is unstable in acid conditions, and therefore, the acid portion should be contained in the first component only. DMSO can be used for this two-component formulation, and it can be added to both formulations at about 50%, replacing about 50% of the water.

Method for Direct Bilirubin Assay

Twenty $\mu$L of sample is mixed with 200 $\mu$L of working reagent and incubated for 4 minutes at 37° C. The absorbance of the mixture is measured with a spectrophotometer at a wavelength between 660–710 nm, against a reagent blank prepared by substituting water for the sample. Preferably, the absorbance measurements are made at a wavelength between 700–710 nm, most preferably, at 700 nm. An aqueous protein-based bilirubin standard is measured against a reagent blank to calibrate the system. The net absorbance is determined by subtracting the reagent blank absorbance from the test absorbance. The results are calculated by comparing the net absorbance (net of reagent blank reading) of the unknown sample to the net absorbance (net of reagent blank reading) of the similarly-treated standard, by the following equation:

Concentration of unknown =

$$\frac{A_{test\ sample} - A_{reagent\ blank}}{A_{test\ standard} - A_{reagent\ blank}} \times \text{Concentration of standard.}$$

When increased turbidity is present, bichromatic correction and/or a dynanmic sample blank should be utilized to minimize the effects of the turbidity. When bichromatic correction is utilized, a second absorbance reading is preferably taken at a secondary bichromatic wavelength of 740–800 nm. When bichromatic correction is utilized, the respective absorbances (A) of the test sample, the reagent blank and the test standard are spectrophotometrically measured at a primary wavelength (1°$\lambda$) as described above, and at a secondary wavelength (2°$\lambda$). The concentration of direct bilirubin in the test sample is calculated by the equation:

Conc. of unknown =

$$\frac{(A_{tst\ sample1^{\circ}\lambda} - A_{rgt\ blk1^{\circ}\lambda}) - (A_{tst\ sample2^{\circ}\lambda} - A_{rgt\ blk2^{\circ}\lambda})}{(A_{tst\ std1^{\circ}\lambda} - A_{rgt\ blk1^{\circ}\lambda}) - (A_{tst\ std2^{\circ}\lambda} - A_{rgt\ blk2^{\circ}\lambda})} \times \text{conc. of std.}$$

If the spectrophotometric instrumentation is not capable of performing a measurement at the secondary bichromatic wavelength, a dynamic blank should be used. In this case, a 2-component reagent is used for the sample and the standard. In order to perform the dyinamic blank, approximately 250 $\mu$L of the first reagent component is mixed with 18 $\mu$L of the sample of bodily fluid. A first absorbance measurement $A_{test1}$ is made after 1–2 minutes. Then 50 $\mu$L of the second reagent component is added and a second absorbance reading $A_{test2}$ is made after an incubation time of about 4–8 minutes. The concentration of direct reacting bilirubin is calculated by comparing the differential absorbance of the sample with that for a similarly treated and measured known bilirubin standard, such as Synermed® IRCal, available from Synermed Inc. of Montreal (Lachine), Canada, which has been assayed by the Jendrassik and Grof reference method for direct bilirubin.

A volume correction may be performed as described above for the total bilirubin assay.

The amount of direct reacting bilirubin is calculated according to the following equation:

$$\text{Conc. of unknown} = \frac{A_{test2} - (A_{tst1} \times \text{Vol. factor})}{A_{std2} - (A_{std1} \times \text{Vol. factor})} \times \text{conc. of the std.}$$

Another type of correction that may be used with some analyzers such as the Synermed® IR200 in a direct bilirubin assay is a sample blank. When a sample blank is utilized, the sample is added to the single reagent and immediately (within 5 seconds) a first reading ($RS_i$) is taken before the reaction has proceeded. A second reading (RS) is then taken at the end of the reaction. By taking a quick reading of the sample, any endogenous interferants in the sample are blanked out ($RS_i$-$RS_f$) such that only the net absorbance developed from the conjugated bilirubin is measured.

Parameter settings for an automated application for the Synermed® IR200 are as follows:

| IR200 CHEMISTRY PARAMETERS | |
|---|---|
| Test Name: | Dir. Bilirubin: |
| Sample volume: | 25 $\mu$L |
| Reagent volume: | 220 $\mu$L |
| Blank: | Sample |
| Incubate: | 390 sec. |
| Wavelength: | 700 nm |

-continued

IR200 CHEMISTRY PARAMETERS

| Test Name: | Dir. Bilirubin: |
|---|---|
| 2nd wavelength: | None |
| Max life: | 400 |

The automated application may be made using a dynamic blank with the following application parameters for the Synermed® IR500:

| Type: | End point |
|---|---|
| First reagent Vol. (μL): | 250 |
| Second rgt Vol. (μL): | 50 |
| Sample Volume (μL) | 18 |
| Primary wavelength | 710 nm |
| Delay for rgt 2 dispense | 1:12 |
| Reaction delay | 3:12 |
| High Reagent Blank: | 3.5000 |
| Maximum Deviation: | 0.5000 |

What is claimed is:

1. A method for the assay of total bilirubin in a sample of bodily fluid, comprising the steps of:
    providing a test reagent, said test reagent comprising (1) a solvent for solubilizing the total bilirubin and proteins in said sample, (2) an acid, and (3) a promoter for promoting the oxidation of the total bilirubin in the sample and the formation of a light-absorbing bitirubin-chromophore detectable in the near-infrared region of the spectrum;
    preparing a test sample by mixing said test reagent with said sample of bodily fluid;
    preparing a reagent blank by mixing said test reagent with water;
    preparing a test standard by mixing said test reagent with a bilirubin standard of known total bilirubin concentration;
    spectrophotometrically measuring the absorbances (A) of the test sample, the reagent blank and the test standard at a wavelength between about 650 and 710 nm; and
    calculating the concentration of total bilirubin in the test sample by the equation:

Concentration of Unknown =

$$\frac{A_{test\ sample} - A_{reagent\ blank}}{A_{test\ standard} - A_{reagent\ blank}} \times \text{Concentration of the standard.}$$

2. The method of claim 1, wherein the wavelength is about 700 to 710 nm.

3. The method of claim 1, wherein said test sample, reagent blank and test standard are incubated for 4–8 minutes at 37° C. prior to measuring said absorbances.

4. The method of claim 1, wherein said solvent comprises dimethyl sulfoxide with or without 10% (v/v) water, said acid comprises a member selected from the group consisting of hydrochloric acid, nitric acid and sulfuric acid, and said promoter comprises a member selected from the group consisting of nitrite ion, cupric ion, ferric ion, ferricyanide ion and cupric-lodide, and wherein said absorbance is about 700 to 710 nm.

5. The method of claim 1, wherein said solvent comprises water with or without about 5% (v/v) detergent, and wherein said absorbance is measured at about 650 nm.

6. The method of claim 1, wherein the solvent comprises dimethyl sulfoxide, dimethyl formamide, ethylene glycol, an ethylene glycol ether, a lower alkyl alcohol, or mixtures of the foregoing.

7. The method of claim 1, wherein the solvent comprises dimethyl sulfoxide, with or without up to about 10% water (v/v).

8. The method of claim 1, wherein the solvent comprises dimethyl sulfoxide as a first component, and a second component comprising water containing about 5% of a nonionic or zwitterionic detergent, the ratio of said first component to said second component being about 90:10 or greater.

9. A method for the assay of total bilirubin in a sample of bodily fluid, comprising the steps of:
    providing a test reagent, said test reagent comprising (1) a solvent for solubilizing the total bilirubin and proteins in said sample, (2) an acid, and (3) a promoter for promoting the oxidation of the total bilirubin in the sample and the formation of a light-absorbing bilirubin-chromophore detectable in the near-infrared region of the spectrum;
    preparing a test sample by mixing said test reagent with said sample of bodily fluid;
    preparing a reagent blank by mixing said test reagent with water;
    preparing a test standard by mixing said test reagent with a bilirubin standard of known total bilirubin concentration;
    spectrophotometrically measuring the absorbances (A) of the test sample, the reagent blank and the test standard at a primary wavelength (1°λ) between about 650 and 710 nm, and at a secondary wavelength (2°λ) between about 740 and 800 nm; and
    calculating the concentration of total bilirubin in the test sample by the equation:

Conc. of unknown =

$$\frac{(A_{tst\ sample1°\lambda} - A_{rgt\ blk1°\lambda}) - (A_{tst\ sample2°\lambda} - A_{rgt\ blk2°\lambda})}{(A_{tst\ std1°\lambda} - A_{rgt\ blk1°\lambda}) - (A_{tst\ std2°\lambda} - A_{rgt\ blk2°\lambda})} \times \text{Conc. of std.}$$

10. The method of claim 9, wherein said primary wavelength (1°λ) is about 700–710 nm.

11. The method of claim 9, wherein said test sample, reagent blank and test standard are incubated for 4–8 minutes prior to measuring said absorbances.

12. A method for the assay of total bilirubin in a sample of bodily fluid, comprising the steps of:
    providing a two-component reagent, a first one of said components including a bilirubin solvent and an acid but not including a promoter, and a second one of said components including said solvent and a promoter for promoting oxidation of bitirubin and formation of a light-absorbing bilirubin-chromophore detectable in the near-infrared region of the spectrum;
    adding said sample to said first component, and measuring the absorbance $A_{test1}$ of the mixture within 1–2 minutes;
    adding said second component to the mixture of the sample and the first component, and measuring the absorbance $A_{test2}$ after 4–8 minutes;
    adding a standard of known total bilirubin concentration to said first component, and measuring the absorbance $A_{std1}$ of the mixture within 1–2 minutes;

adding said second component to the mixture of the standard and said first component, and measuring the absorbance $A_{std2}$ after 4–8 minutes;

providing a volume correction factor to account for the increased volume when respective $A_{test2}$ and $A_{std2}$ measurements are taken compared to the lesser volumes when $A_{test1}$ and $A_{std1}$ measurements are taken; and calculating the concentration of bilirubin in the test sample according to the following equation:

$$\text{Conc. of unknown} = \frac{A_{test2} - (A_{test1} \times \text{Vol. factor})}{A_{std2} - (A_{std1} \times \text{Vol. factor})} \times \text{conc. of standard,}$$

wherein $A_{test1}$, $A_{test2}$, $A_{std1}$ and $A_{std2}$ are measured in the near-infrared region of the spectrum.

13. A reagent for the assay of total bilirubin in a sample of bodily fluid, the reagent comprising:
a solvent for solubilizing the total bilirubin and proteins in said sample;
an acid; and
a promoter for promoting the oxidation of the total bilirubin in the sample, and the formation of a light-absorbing bilirubin-chromophore detectable in the near-infrared region of the spectrum between about 650 and 710 nm.

14. The reagent of claim 13, wherein the solvent comprises dimethyl sulfoxide, dimethyl formamide, ethylene glycol, an ethylene glycol ether, a lower alkyl alcohol, or mixtures of the foregoing.

15. The reagent of claim 13, wherein the solvent comprises dimethyl sulfoxide, with or without up to about 10% water (v/v).

16. The reagent of claim 13, wherein the solvent comprises dimethyl sulfoxide as a first component, and a second component comprising water containing about 5% of a nonionic or zwitterionic detergent, the ratio of said first component to said second component being about 90:10 or greater.

17. The reagent of claim 16, wherein said detergent comprises a member selected from the group consisting of polyoxyethylene 23 lauryl ether, octoxynol-9, octoxynol-10, and cocoamidopropyl-N,N-dimethyl-N-2-hydroxypropylsulfobetaine, and mixtures thereof.

18. The reagent of claim 13, wherein said acid comprises a member selected from the group consisting of hydrochloric acid, nitric acid, sulfuric acid and mixtures thereof, and said acid concentration is 0.05–0.1 N.

19. The reagent of claim 13, wherein said promoter comprises one or more ions having an oxidation potential expressed as single electrode potential E° from about 1.00 to about 0.34 volts.

20. The reagent of claim 13, wherein said promoter is a member selected from the group consisting of nitrite ion, ferricyanide ion, ferric ion, cupric ion, and cupric-iodide ion, and mixtures thereof.

21. The reagent of claim 13, wherein the solvent is dimethyl sulfoxide, the acid is hydrochloric acid and the promoter is copper sulfate.

22. The reagent of claim 21, wherein the components are present in the following amount, per liter of reagent: 900 ml dimethyl sulfoxide; 5 ml concentrated hydrochloric acid, 0.37 gm copper sulfate and 95 ml water.

23. The reagent of claim 13, wherein the reagent comprises a first and a second component, said first component including said acid, and said second component including said promoter, said solvent being present in either or both of said first and second components.

24. A method for the assay of direct bilirubin in a sample of bodily fluid containing conjugated and unconjugated bilirubin, and proteins, comprising the steps of:
providing a test reagent for mixing with said sample to form a near-infrared absorbing chromophore for conjugated bilirubin while forming chromophores with unconjugated bilirubin having substantially no near-infrared color, said test reagent comprising (1) an aqueous component containing an acid for solubilizing the conjugated and unconjugated bilirubin and the proteins present in the sample, and (2) a promoter for promoting the oxidation of conjugated bilirubin in the sample to a light-absorbing bilirubin chromophore in the near-infrared region of the spectrum while promoting very little oxidation of unconjugated bilirubin;
preparing a test sample by mixing said test reagent with said sample of bodily fluid;
preparing a reagent blank by mixing said test reagent with water;
preparing a test standard by mixing said test reagent with a bilirubin standard of known conjugated bilirubin concentration;
incubating said test sample and test standard for a period of time sufficient to oxidize said conjugated bilirubin, and not to oxidize said unconjugated bilirubin;
spectrophotometrically measuring the absorbances (A) of the test sample, the reagent blank and the test standard in the near-infrared region of the spectrum; and
calculating the concentration of direct bilirubin in the test sample by the equation:

$$\text{Conc. of unknown} = \frac{A_{test\,sample} - A_{reagent\,blank}}{A_{test\,standard} - A_{reagent\,blank}} \times \text{Conc. of standard.}$$

25. The method of claim 24, wherein said absorbances (A) are measured at a wavelength between about 660 and 710 nm.

26. The method of claim 25, wherein the wavelength is between 700 and 710 nm.

27. The method of claim 24, wherein said test sample, reagent blank and test standard are incubated for about 4 minutes at 37° C. prior to measuring said absorbances.

28. The method of claim 24, wherein said reagent further comprises a surfactant selected from the group consisting of polyoxyethylene 23 lauryl ether, octoxynol-9, octoxynol-10, and mixtures thereof.

29. The method of claim 24, wherein said aqueous component further comprises about 50% (v/v) dimethyl sulfoxide.

30. The method of claim 24, wherein said promoter comprises one or more ions having an oxidation potential expressed as a single electrode potential E° from about 0.78 to about 0.34 volts.

31. The method of claim 30, wherein said promoter is a member selected from the group consisting of ferricyanide ion, ferric ion, cupric ion and mixtures thereof.

32. The method of claim 24, wherein said acid comprises a member selected from the group consisting of hydrochloric acid, nitric acid, sulfuric acid and mixtures thereof, and said acid concentration is 0.06–0.6 N.

33. A method for the assay of direct bilirubin in a sample of bodily fluid containing conjugated and unconjugated bilirubin, and proteins, comprising the steps of:

providing a test reagent for mixing with said sample to form a near-infrared absorbing chromophore for conjugated bilirubin while forming chromophores with unconjugated bilirubin having substantially no near-infrared color, said test reagent comprising (1) an aqueous component containing an acid for solubilizing the conjugated and unconjugated bilirubin and the proteins present in the sample, and (2) a promoter for promoting the oxidation of conjugated bilirubin in the sample to a light-absorbing bilirubin chromophore in the near-infared region of the specturm while promoting very little oxidation of unconjugated bilirubin;

preparing a test sample by mixing said test reagent with said sample of bodily fluid;

preparing a reagent blank by mixing said test reagent with water;

preparing a test standard by mixing said test reagent with a bilirubin standard of known conjugated bilirubin concentration;

incubating said test sample and test standard for a period of time sufficient to oxidize said conjugated bilirubin, and not to oxidize said unconjugated bilirubin;

spectrophotometrically measuring the absorbances (A) of the test sample, the reagent blank and the test standard at a primary wavelength ($1°\lambda$) and at a secondary wavelength ($2°\lambda$) both in the near-infrared region of the spectrum; and calculating the concentration of direct bilirubin in the test sample by the equation:

$$\text{Conc. of unknown} = \frac{(A_{tst\,sample\,1°\lambda} - A_{rgt\,blk\,1°\lambda}) - (A_{tst\,sample\,2°\lambda} - A_{rgt\,blk\,2°\lambda})}{(A_{tst\,std\,1°\lambda} - A_{rgt\,blk\,1°\lambda}) - (A_{tst\,std\,2°\lambda} - A_{rgt\,blk\,2°\lambda})} \times \text{conc. of std.}$$

34. A method for the assay of direct bilirubin in a sample of bodily fluid, comprising the steps of:

providing a test reagent for mixing with said sample to form a near-infrared absorbing chromophore for conjugated bilirubin while forming chromophores with unconjugated bilirubin having substantially no near-infrared color, said test reagent comprising a two-component reagent, a first one of said components including a bilirubin solvent and an acid but not including a promoter, and a second one of said components including said solvent and a promoter for promoting oxidation of conjugated bilirubin and formation of a light-absorbing bilirubin-chromophore detectable in the near-infrared region of the spectrum;

adding said sample to said first component, and measuring the absorbance $A_{test1}$ of the niixture within 1–2 minutes;

adding said second component to the mixture, and measuring the absorbance $A_{test2}$ after 4–8 minutes;

adding a standard of known total bilirubin concentration to said first component, and measuring the absorbance $A_{std}$ of the mixture within 1–2 minutes;

adding said second component to the mixture of the standard and said first component, and measuring the absorbance $A_{std2}$ after 4–8 minutes;

providing a volume correction factor to account for the increased volume when respective $A_{test2}$ and $A_{std2}$ measurements are taken compared to the lesser volumes when $A_{test1}$ and $A_{std1}$ measurements are taken; and calculating the concentration of direct bilirubin in the test sample according to the following equation:

$$\text{Conc. of unknown} = \frac{A_{test2} - [(A_{test1}) \times \text{Vol. factor})]}{A_{std2} - [(A_{std1}) \times \text{Vol. factor})]} \times \text{conc. of the std,}$$

wherein $A_{test1}$, $A_{test2}$, $A_{std1}$ and $A_{std2}$ are measured in the near-infrared region of the spectrum.

35. A reagent for assay of conjugated bilirubin in a sample of bodily fluid containing conjugated and unconjugated bilirubin, and proteins, comprising:

an aqueous component containing an acid for solubilizing the conjugated and unconjugated bilirubin and the proteins present in the sample, and a promoter for oxidizing said conjugated bilirubin in the sample, said acid and said promoter being present in said reagent in amounts sufficient to oxidize the conjugated bilirubin in the sample to a light-absorbing bilirubin chromophore in the near-infrared region of the spectum while promoting very little oxidation of unconjugated bilirubin.

36. The reagent of claim 35, wherein the aqueous component further includes approximately 50% dimethyl sulfoxide (v/v), said acid comprises a member selected from the group consisting of hydrochloric acid, nitric acid and sulfuric acid, and said acid concentration is 0.06–0.6 N, and wherein said promoter comprises at least one of ferricynanide ion, cupric ion and ferric ion.

37. The reagent of claim 36, further comprising a surfactant, said surfactant comprising a member selected from the group consisting of polyoxyethylene 23 lauryl ether, octoxynol-9, octoxynol-10, and mixtures thereof.

38. The reagent of claim 37, wherein said acid comprises 0.16 N HCl and said promoter comprises 3 mM cupnic ion.

39. The reagent of claim 35, wherein the promoter comprises at least one of ferricyanide ion, ferric ion and cupric ion.

40. A diagnostic test kit for the assay of total bilirubin and direct reacting bilirubin in a sample, said test kit comprising:

a first composition comprising (1) a solvent for solubilizing the total bilirubin and proteins in said sample, (2) an acid, and (3) a promoter for promoting the oxidation of the total bilirubin in the sample and the formation of a light-absorbing bilirubin-chromophore detectable in the near-infrared region of the spectrum; and a second composition comprising an aqueous component containing an acid for solubilizing the conjugated and unconjugated bilirubin and the proteins present in the sample, and a promoter for oxidizing said conjugated bilirubin in the sample, said acid and said promoter being present in said second composition in amounts sufficient to oxidize the conjugated bilirubin in the sample to a light-absorbing bilirubin chromophore in the near-infrared region of the spectrum while promoting very little oxidation of unconjugated bilirubin.

41. The diagnostic kit of claim 40, wherein in said first composition said solvent comprises a member selected from the group consisting of dimethyl sulfoxide, dimethyl formamide, ethylene glycol, an ethylene glycol ether, a lower alkyl alcohol, and mixtures thereof; said acid comprises a member selected from the group consisting of hydrochloric acid, nitric acid, sulfuric acid and mixtures thereof, and said promoter comprises one or more ions having an oxidation potential expressed as single electrode potential E° from about 1.00 to about 0.34 volts.

42. The diagnostic kit of claim 41, wherein said first composition further comprises a member selected from the group consisting of polyoxyethylene 23 lauryl ether, octoxynol-9, octoxynol-10, and cocoamidopropyl-N,N-dimethyl-N-2-hydroxypropylsulfobetaine, and mixtures thereof.

43. The diagnostic kit of claim 40, wherein said second composition further includes approximately 50% dimethyl sulfoxide (v/v), and a surfactant, said surfactant comprising a member selected from the group consisting of polyoxyethylene 23 lauryl ether, octoxynol-9, octoxynol-10, and mixtures thereof.

44. The diagnostic kit of claim 40, wherein the promoter in said second composition comprises one or more ions having an oxidation potential expressed as single electrode potential E° from about 0.78 to about 0.34 volts.

45. The diagnostic kit of claim 44, wherein the promoter in said second composition comprises at least one of ferricyanide ion, ferric ion and cupric ion.

46. The diagnostic kit of claim 40, wherein said first composition of said test kit is supplied as respective first and second components, said first component comprising said acid and said second component comprising said promoter.

47. The diagnostic kit of claim 40, wherein said second composition of said test kit is supplied as respective first and second components, said first component comprising said acid and said second component comprising said promoter.

* * * * *

UNITED STATES PATENT AND TRADEMARK OFFICE
CERTIFICATE OF CORRECTION

PATENT NO. : 6,326,208 B1
DATED : December 4, 2001
INVENTOR(S) : Denney

It is certified that error appears in the above-identified patent and that said Letters Patent is hereby corrected as shown below:

Column 1,
Line 23, please delete the word "unconijuated" and insert -- unconjugated --.
Lines 33 and 34, please delete the word "hernolytic" and insert -- hemolytic --.
Line 67, please delete the word "the" and insert thereof the word -- die --.

Column 2,
Line 7, please delete the word "liepatobiliary" and insert -- hepatobiliary --.
Line 57, please delete the word "losing" and insert thereof the word -- using --.

Column 3,
Line 7, please delete the word "azostilfanilic" and insert -- azosulfanilic --.
Line 14, please delete the word "dichlorophieniyl" and insert -- dichlorophenyl --.
Line 30, please delete "(198(" and insert thereof -- (1986) --; and delete the word "enmbo(lying" and insert -- embodying --.
Line 35, please delete the word "destriction" and insert -- destruction --.
Line 67, please delete the word "tip" and insert thereof -- up --.

Column 4,
Line 44, please delete the word "Thle" and insert -- The --.

Column 5,
Line 18, please delete the word "formanide" and insert -- formamide --.
Line 20, please delete the word "monometlhyl" and insert -- monomethyl --.
Line 22, please delete the word "miscibile" and insert the word -- miscible --.
Line 28, please delete the letter "e" and insert thereof the word -- the --.

Column 6,
Line 27, please delete the word "sticcinic" and insert -- succinic --.

Column 7,
Line 17, please delete the word "chromophlore" and insert -- chromophore --.
Line 30, please delete the word "fenicyanide" and insert -- ferricyanide --.

Column 8,
Line 7, please delete the word "moles" and insert thereof -- μmoles --.
Line 35, please delete the word "glutathionie" and insert -- glutathione --.

UNITED STATES PATENT AND TRADEMARK OFFICE
CERTIFICATE OF CORRECTION

PATENT NO. : 6,326,208 B1
DATED : December 4, 2001
INVENTOR(S) : Denney

It is certified that error appears in the above-identified patent and that said Letters Patent is hereby corrected as shown below:

Column 12,
Line 63, please delete the word "analyzers" and insert -- analyzer --.

Column 13,
Line 61, please delete the word "optimnal" and insert -- optimal --.

Column 14,
Line 58, please delete the word "10 M" and insert -- 10mM --.

Column 16,
Line 52, please delete the word "subtittited" and insert -- substituted --.

Column 18,
Line 21, please delete the word "dyinamic" and insert thereof the word -- dynamic --.
Line 49, please delete the word "(RS)" and insert -- $(RS_f)$ --.

Column 19,
Line 32, please delete the word "bitirubin-" and insert the word -- bilirubin --.
Line 63, please delete the word "cupric-Iodide" and insert -- cupric-iodide --.

Column 23,
Line 52, please delete the word "niixture" and insert -- mixture --.

Signed and Sealed this

Ninth Day of April, 2002

*Attest:*

*Attesting Officer*

JAMES E. ROGAN
*Director of the United States Patent and Trademark Office*